(12) United States Patent
Walsh et al.

(10) Patent No.: US 11,045,083 B2
(45) Date of Patent: Jun. 29, 2021

(54) FLASH OPTIMIZATION DURING RETINAL BURST IMAGING

(71) Applicant: Verily Life Sciences LLC, Mountain View, CA (US)

(72) Inventors: Corey Walsh, Cambridge, MA (US); Eliezer Glik, San Francisco, CA (US); Sam Kavusi, Menlo Park, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 295 days.

(21) Appl. No.: 16/151,022

(22) Filed: Oct. 3, 2018

(65) Prior Publication Data

US 2019/0110677 A1 Apr. 18, 2019

Related U.S. Application Data

(60) Provisional application No. 62/573,324, filed on Oct. 17, 2017.

(51) Int. Cl.
| | | |
|---|---|---|
| *A61B 3/00* | (2006.01) | |
| *A61B 3/14* | (2006.01) | |
| *A61B 3/12* | (2006.01) | |

(52) U.S. Cl.
CPC ............. *A61B 3/0008* (2013.01); *A61B 3/12* (2013.01); *A61B 3/14* (2013.01); *G06T 2207/30041* (2013.01)

(58) Field of Classification Search
CPC .......... G02B 27/017; G02B 2027/0187; G02B 2027/014; G02B 2027/0178;
(Continued)

(56) References Cited

U.S. PATENT DOCUMENTS

| 4,834,528 A | 5/1989 | Howland et al. |
|---|---|---|
| 6,733,129 B2 | 5/2004 | Masaki |
| | (Continued) | |

FOREIGN PATENT DOCUMENTS

| JP | 2017099717 A | 6/2017 |
|---|---|---|
| WO | 2017/127798 A1 | 7/2017 |

OTHER PUBLICATIONS

International Search Report and Written Opinion from the International Searching Authority dated Jan. 2, 2019 for International Application No. PCT/US2018/054965, filed Oct. 9, 2018, 7 pages.
(Continued)

*Primary Examiner* — Brandi N Thomas
(74) *Attorney, Agent, or Firm* — Christensen O'Connor Johnson Kindness PLLC

(57) ABSTRACT

An apparatus for imaging an interior of an eye includes a light sensitive sensor, a plurality of light emitters (LEs) capable of outputting light, a plurality of nonvisible light emitters (NV-LEs) capable of outputting nonvisible light, and a controller. The controller is coupled to the plurality of LEs, the plurality of NV-LEs, and the light sensitive sensor, and the controller implements logic that when executed by the controller causes the apparatus to perform operations. The operations include illuminating the eye with the nonvisible light from the plurality of NV-LEs, and determining an amount of reflection of the nonvisible light from the eye for each of the NV-LEs in the plurality of NV-LEs. The operations also include illuminating the eye with selected one or more of the LEs in the plurality of LEs, and capturing, with the light sensitive sensor, a sequence of images of the interior of the eye while the eye is illuminated with the light from the LEs.

25 Claims, 8 Drawing Sheets

(58) Field of Classification Search
CPC .... G02B 2027/0138; G02B 2027/0127; G02B 27/0093; G02B 27/0172; G02B 2027/0134; G02B 2027/0141; G02B 2027/0159; G02B 27/0101; G02B 27/0149; G02B 3/14; G02B 2027/0118; G02B 3/0081; G02B 6/00; G02B 2027/0147; G02B 2027/0185; G02B 21/00; G02B 25/00
USPC ........ 351/200, 205–206, 209–211, 221–223, 351/243–246
See application file for complete search history.

(56) References Cited

U.S. PATENT DOCUMENTS

| | | | |
|---|---|---|---|
| 6,839,128 B2 | 1/2005 | Premjeyanth et al. | |
| 7,307,785 B2 | 12/2007 | Obrebski et al. | |
| 7,458,685 B2 | 12/2008 | Liang et al. | |
| 7,499,634 B2 | 3/2009 | Yogesan et al. | |
| 7,878,653 B2* | 2/2011 | Ichikawa | A61B 3/14 351/210 |
| 7,954,949 B2 | 6/2011 | Suzuki | |
| 8,408,464 B2 | 4/2013 | Zhu et al. | |
| 8,684,529 B2 | 4/2014 | Johansson et al. | |
| 8,811,657 B2 | 8/2014 | Teiwes et al. | |
| 8,955,971 B2 | 2/2015 | Ichikawa et al. | |
| 9,125,559 B2 | 9/2015 | Kersting et al. | |
| 9,271,646 B2 | 3/2016 | Neal et al. | |
| 9,289,122 B2 | 3/2016 | Chinnock et al. | |
| 9,314,157 B2 | 4/2016 | Yao et al. | |
| 9,498,126 B2 | 11/2016 | Wang | |
| 9,918,629 B2 | 3/2018 | Wang | |
| 2013/0010259 A1 | 1/2013 | Carnevale | |
| 2013/0057828 A1 | 3/2013 | de Smet | |
| 2013/0112880 A1* | 5/2013 | Katoh | G06F 3/0412 250/349 |
| 2013/0193847 A1 | 8/2013 | Recker et al. | |
| 2013/0194548 A1 | 8/2013 | Francis et al. | |
| 2013/0208241 A1 | 8/2013 | Lawson et al. | |
| 2013/0208243 A1 | 8/2013 | Sakagawa | |
| 2013/0329189 A1 | 12/2013 | Mizucchi | |
| 2014/0240666 A1 | 8/2014 | Ootsuki | |
| 2015/0125092 A1 | 5/2015 | Zhuo et al. | |
| 2016/0174838 A1 | 6/2016 | Herranen et al. | |
| 2016/0302665 A1 | 10/2016 | Swedish et al. | |
| 2016/0317031 A1 | 11/2016 | Yang et al. | |
| 2016/0338589 A1 | 11/2016 | Carrasco-Zevallos et al. | |
| 2018/0084989 A1* | 3/2018 | Su | H04N 5/23206 |

OTHER PUBLICATIONS

DeHoog et al., "Optimal parameters for retinal illumination and imaging in fundus cameras," Applied Optics, vol. 47, No. 36, Dec. 20, 2008, 2008 Optical Society of America, pp. 6769-6777.

Matos et al., "Coaxial fundus camera for ophthalmology," Proc. of SPIE vol. 9578, 2015, 5 pages.

TRC-NW8 Non-Mydriatic Retinal Camera, Topcon Medical Systems, Inc., http:www.topconmedical.com/products/trcnw8.htm, Accessed Aug. 31, 2016, 1 page.

Tran et al., "Construction of an Inexpensive, Hand-Held Fundus Camera through Modification of a Consumer 'Point-and-Shoot' Camera," Investigative Ophthalmology & Visual Science, Nov. 2012, vol. 53, No. 12, 10 pages.

CenterVue Homepage, http://www.centervue.com/, Accessed Aug. 31, 2016, 5 pages.

Swedish et al., "eyeSelfie: Self Directed Eye Alignment using Reciprocal Eye Box Imaging," MIT Media Lab—Camera Culture Group, http:web.media.mit.edu/~tswedish/projects/eyeSelfie.html, Accessed Aug. 31, 2016, 3 pages.

Sugita et al., "Motion artifact and speckle noise reduction in polarization sensitive optical coherence tomography by retinal tracking," Biomedical Optics Express, vol. 5, No. 1, Jan. 1, 2014, pp. 106-122.

Bengtsson et al., "A new generation of algorithms for computerized threshold perimetry, SITA," Acta Ophthalmologica Scandinavica 1997, vol. 75, pp. 368-375.

Fan et al., "Modeling Transient Pupillary Light Reflex Induced by a Short Light Flash," IEEE Transactions on Biomedical Engineering, vol. 58, No. 1, Jan. 2011, 7 pages.

* cited by examiner

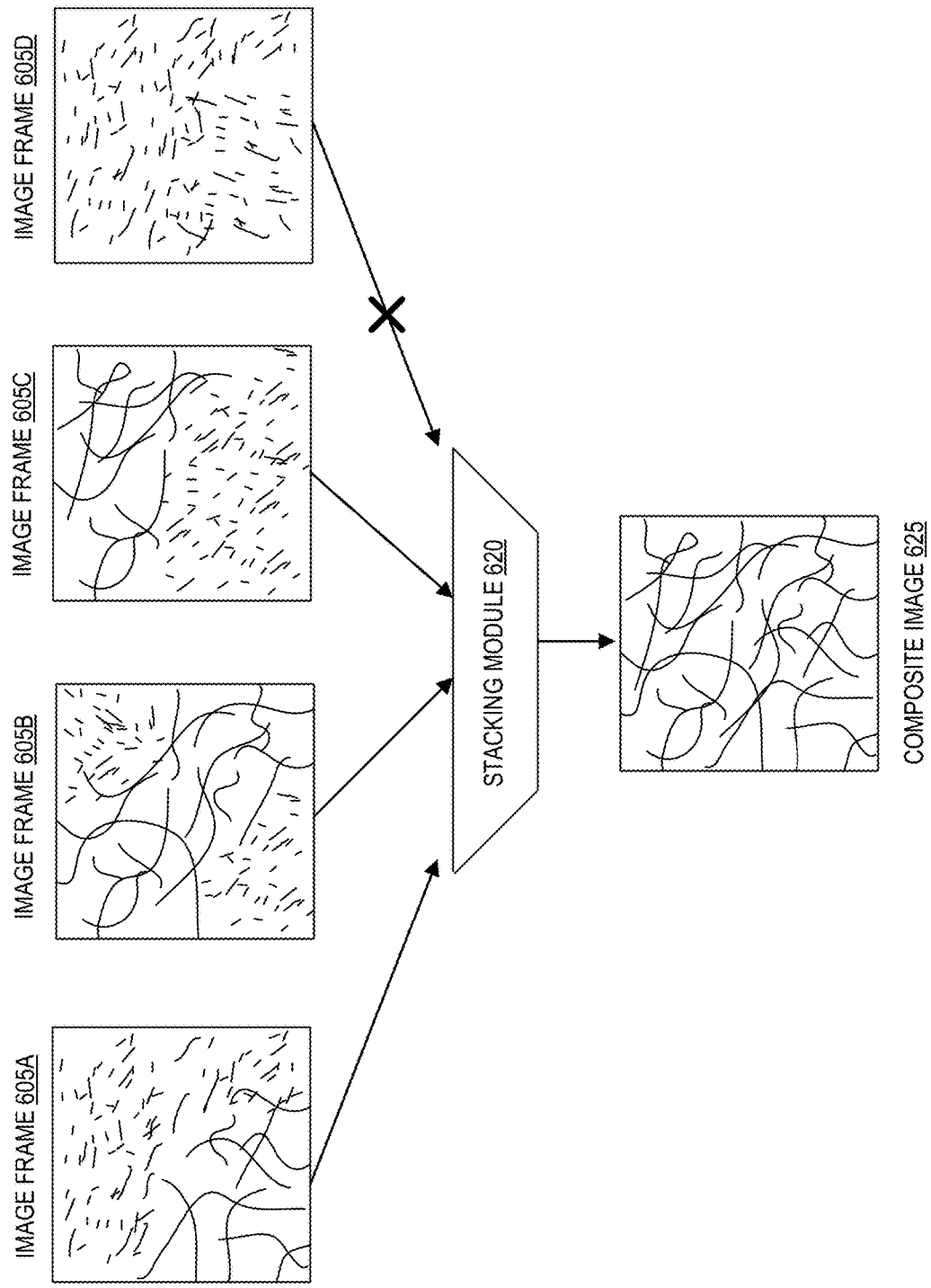

FLASH OPTIMIZATION DURING RETINAL BURST IMAGING

REFERENCE TO RELATED APPLICATION

This application claims the benefit of U.S. Application No. 62/573,324, filed on Oct. 17, 2017, the contents of which are incorporated herein by reference.

TECHNICAL FIELD

This disclosure relates generally to imaging technologies, and in particular, relates to retinal imaging.

BACKGROUND INFORMATION

Retinal imaging is a part of basic eye exams for screening, field diagnosis, and progress monitoring of many retinal diseases. A high fidelity retinal image is important for accurate screening, diagnosis, and monitoring. Bright illumination of the posterior interior surface of the eye (i.e., retina) through the pupil improves image fidelity while often creating optical aberrations or image artifacts, such as lens flare. Lens flare is a phenomenon where light scatters off of interior components of a lens system due to internal reflections, refractive index changes at various internal boundaries, imperfections, or otherwise. This scattered light shows up in the retinal image as lens flare, which is deleterious to the image quality. The brighter the illumination, the more pronounced the lens flare, which undermines the goal of improving image fidelity. Other image artifacts may arise due to corneal reflections or iris reflections from misalignment with the pupil.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 6 illustrates focus stacking images of an iris, in accordance with an embodiment of the disclosure.

DETAILED DESCRIPTION

Figure 1A:
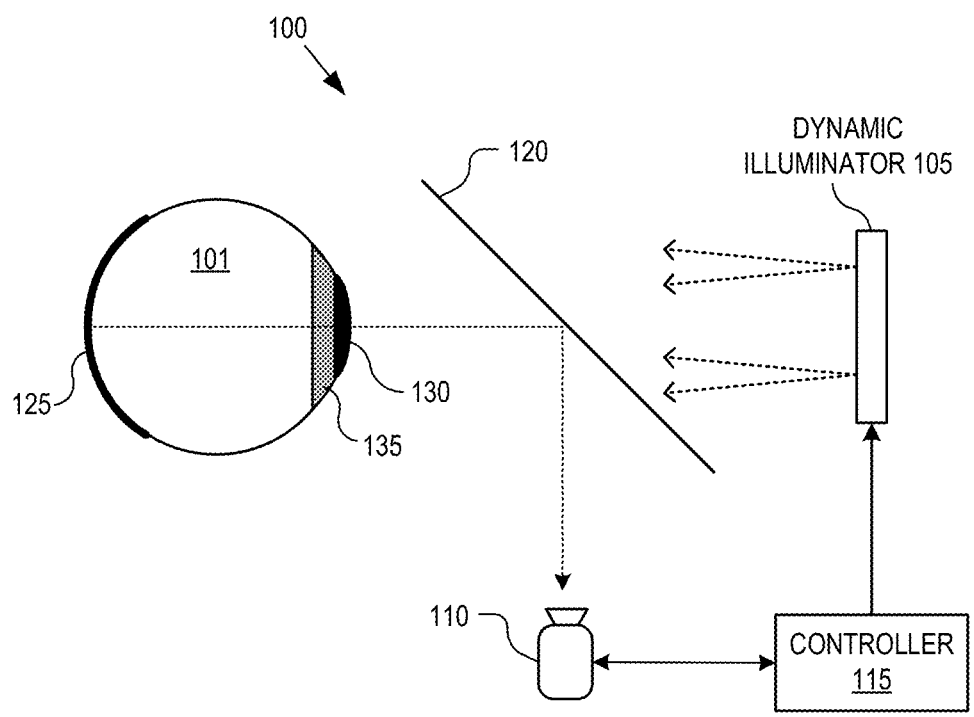
FIG. 1A illustrates a system for imaging an interior of an eye, in accordance with an embodiment of the disclosure.

Embodiments of a system, apparatus, and method of flash optimization during retinal burst imaging are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

High fidelity retinal images are important for screening, diagnosing, and monitoring many retinal diseases. To this end, reducing or eliminating instances of image artifacts (e.g., deleterious corneal reflections, etc.) that occlude, or otherwise malign portions of the retinal image is desirable. Embodiments described herein describe systems and methods for reducing ocular reflection when imaging the interior of an eye. The images captured are combined to form a composite image of the interior of the eye (e.g., iris). Using images that have fewer defects reduces the number of images that need to be captured, and also reduces the processing power needed to produce a quality composite image.

In some embodiments, a modular printed circuit board (PCB) mount may be used for an illumination assembly to image the eye. Multiple visible flash sources may be mounted on the PCB and it may be necessary quickly determine which lights should fire (e.g., turning on the light source for a short temporal duration, and then turning off the light source). Firing the visible flash sources either sequentially or randomly will likely give at least one good frame (e.g., an in-focus, well-exposed, frame), but will also provide a high fraction of bad frames as well (e.g., out of focus, poorly exposed frames). Here the order and number of flash sources fired to capture image frames is optimized using infrared (IR) pre-illumination and monitoring of respective reflected light from the different positions of IR pre-illuminations.

In several embodiments, multiple IR sources may be located on the PCB as close as possible to the white/visible sources. For example, the housing of each IR source can be in contact with the housing of each white/visible light source, or the IR light and the visible light are emitted from the same diode structure. All of the IR sources may be fired sequentially or randomly, and a controller (e.g., general purpose processor and memory, distributed system, image signal processor, or the like) may determine which of the IR sources produced the fewest reflections and other image defects. The IR reflectance may be correlated to visible (e.g., white light or the like) reflectance. Based on the IR reflections observed, the controller determines which visible flash sources should be fired during visible image capture.

In some embodiments, the image sensor with image processing may be used to detect the IR light reflected back from the eye, and the controller may determine which visible light to fire based on the IR reflections observed by the camera. However, in another or the same embodiment, a collection of photodiodes, located proximate to the visible and IR light emitters, may be used to detect low-reflection frames. Because in some embodiments it is not desirable to capture just the darkest frame (which may be poorly illuminated) it is possible to use color filters on the photodiodes and detect the brightest, mostly-red (since retinas are predominantly red), image. This could be accomplished extremely fast during capture, and potentially better accommodate moving eyes. In some embodiments, the an analog circuitry can control the sequential firing of the IR light emitters, analyze the outputs of the photodiodes in each step of the sequence, and control the firing of the visible light emitters positioned around the image path according to the analysis. In other or the same embodiments, an additional microprocessor, or the retinal camera's existing controller, can be used to accomplish the functionalities of such an analog circuit. In some embodiments, the photodiodes are mounted on the same PCB as the visible and IR light sources. In some embodiments these light detecting photodiodes could be located near or around the image sensor plane. This might help to determine if large reflections are getting to the image plane.

In some embodiment, during pre-capture the subject is being aligned with the optical pathway, and only infrared illumination may be used to image the eye and determine where reflections are originating from. IR reflections may be measured with the camera (or a plurality of photodiodes) and these signals may be received with a controller which determines the IR light sources that produced the reflections. It is appreciated that the IR pre-illumination may happen sequentially by firing each IR light emitter in order, or may happen in a random or other order. The image sensor receives images which are illuminated by infrared, and based on those images (and any other information available) the system can make decisions about how and when to enter subsequent phases. Based on information available in the infrared spectrum, the system will determine a set of white illumination sources to sequentially fire which are expected to yield high quality images. This can be accomplished by sequentially firing the available infrared illuminators and determining a quality metric for each. Then, a model of the optical system may be used to determine a set of white illuminators expected to yield similarly high quality images. It is appreciated that the IR illumination period may be longer or shorter than the visible illumination period, or vice versa, depending on how long it takes to determine which visible light sources will produce quality images.

Since the capture phase is of limited duration, it is important to make any decisions about system configuration in real-time. Any methods which rely on data gathered by the image sensor may be subject to latency induced by data transfer and processing. As stated, one potential method to update flash sequence in real-time is to use a set of photodiodes to infer image quality conditions. Misaligned illumination may be characterized by dark images. Conversely, corneal reflections often involve bright white regions. High quality retinal images are generally of medium brightness and primarily red in hue. Photodiodes with light filters in the imaging pathway could detect these conditions very rapidly (in timescales much shorter than the image sensor exposure), and continuously modify the set of enabled illuminators to optimize for favorable conditions.

Capture may begin when visible LEDs (e.g., white LEDs or other illumination sources such as laser diodes, flash bulbs or the like) in the retinal imaging system turn on. The bright light causes the subject's iris to rapidly close. Accordingly, there is a narrow window of opportunity to gather data which will be later used to construct a retinal image. During this phase it is important to control the system to collect the best data possible. Post-capture begins once the white light has turned off. In this phase, there is time to process the data collected by the system during previous phases.

The following disclosure will describe the embodiments discussed above as they pertain to FIGS. 1A-7.

FIG. 1A illustrates a system 100 for imaging an interior of an eye, in accordance with an embodiment of the disclosure. The illustrated embodiment of imaging system 100 includes a dynamic illuminator 105, a camera 110, a controller 115, and an optical relay system 120 capable of capturing burst image frames of a retina 125 in eye 101. Also shown are iris 135 and pupil 130 of eye 101; light passes through pupil 130 into, and out of, eye 101, and iris 135 may increase or decrease in size depending on light conditions.

Figure 1B:
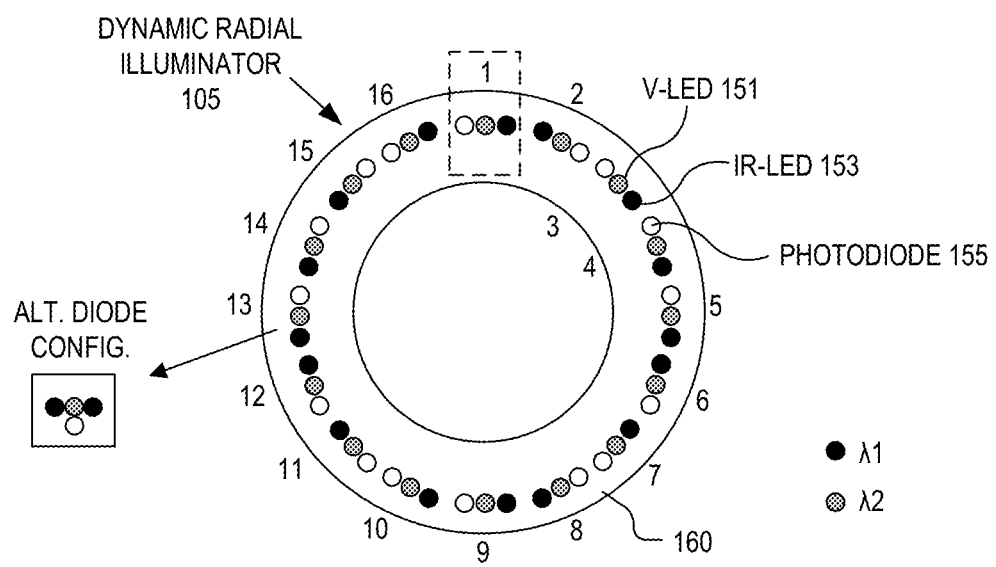
FIG. 1B illustrates a frontal view of a dynamic illuminator included in the apparatus of FIG. 1A, in accordance with an embodiment of the disclosure.

As will be shown in greater detail in connection with FIG. 1B, dynamic illuminator 105 includes a plurality of visible light emitting diodes (V-LEDs) capable of outputting visible light, and plurality of infrared light emitting diodes (IR-LEDs) capable of outputting infrared light. Dynamic illuminator 105, its constituent components, and camera 110 (which may be capable of capturing >240 frames/s) are coupled to controller 115. Controller 115 implements logic that when executed by controller 115 causes system 100 to perform a variety of operations including illuminating eye 101 with the infrared light from the plurality of IR-LEDs, and determining an amount (e.g., intensity, intensity with respect to location or the like) of reflection of the infrared light from eye 101 for each of the IR-LEDs in the plurality of IR-LEDs. System 100 may then illuminate eye 101 with a selected one or more of the V-LEDs in the plurality of V-LEDs based at least in part on the amount of reflection of the infrared light for each of the IR-LEDs. System 100 may then capture, with camera 110, a sequence of images of the interior (e.g., retina) of eye 101 while eye 101 is illuminated with the visible light from the V-LEDs. In other words, in the depicted embodiment, dynamic illuminator 105 may first illuminate eye 101 with IR light, then camera 110 may image the IR light reflected from eye 101. Controller 115 will process the images of the reflected IR light and see where there are reflections that impair image quality. Controller 115 may see what IR-LEDs these reflections came from, and also see which IR-LEDs did not produce a reflection. Controller 115 may then only fire the V-LEDs that are collocated with the IR-LEDs that did not produce a reflection (e.g., disabling some of the V-LEDs when the amount of reflection of the infrared light from a corresponding IR-LED is greater than a threshold reflectance value). Controller 115 may also determine an order of the V-LEDs to illuminate eye 101 with, in response to the amount of reflection of the infrared light from the eye for each of the IR-LEDs. Thus, camera 110 captures visible images of eye 101 that mostly do not contain a reflection.

Since the reflection profile of IR light and visible light from eye 101 may not be the same (e.g., because eye 101 may absorb more IR light than visible light or vice versa), in some embodiments, controller 115 may correlate the amount of reflection of the infrared light from eye 101 for each of the IR-LEDs with a second amount of reflection of the visible light from eye 101 for each of the V-LEDs. In other words, the reflection profile of IR light is correlated to the reflection profile of visible light so the controller knows which V-LEDs to turn on or off after looking at the reflection profile of the IR light.

It is appreciated that dynamic illuminator 105 may emit visible and IR light pulses in any order and even in parallel, and capture images in a similar manner. For example, dynamic illuminator 105 may sequentially fire all of the IR-LEDs, then controller 115 can develop a reflectance profile for all of the IR-LEDs. Then dynamic illuminator 105 can fire the select V-LEDs. However, other embodiments, dynamic illuminator 105 may fire one IR-LED, then one V-LED, etc. In other embodiments, multiple IR-LEDs and V-LEDs may be fired at the same time.

At least some of the visible images captured may be combined to form a composite image using at least one of focus stacking (i.e., combining multiple images taken at different focus distances to give a resulting image with a greater depth of field than any of the individual source images), image stitching (i.e., combining multiple photographic images with overlapping fields of view to produce a segmented panorama or high-resolution image), image blending (i.e. combining a background image and foreground image giving the appearance of partial transparency), or any combination thereof.

In addition to only firing V-LEDs that are likely to produce images with low reflection, it is appreciated that other techniques to filter out poor quality images may be used. For example, a first set of poor quality images may include overexposed images having a luminance value (e.g., an average luminance value across all pixels, or sets of pixels, in the image) greater than a first threshold luminance value, or underexposed images having a luminance value less than a second threshold luminance value. In some embodiments, the images in the first set may not be clearly resolved for other reasons such as the image being too blurry (e.g., because the image sensor moved during capture), the images not containing an image of the retina (e.g., because the subject moved during image capture), or the like. Images may be removed via manual selection or by automated selection (e.g., using high pass/low pass filters to remove images with luminance values that are too high or too low, and/or or using a machine learning algorithm to remove images not including a retina, or the like).

FIG. 1B illustrates a frontal view of dynamic illuminator 105 included in the apparatus of FIG. 1A, in accordance with an embodiment of the disclosure. Dynamic illuminator 105 includes V-LEDs 151, IR-LEDs 153, and photodiodes 155 (capable of absorbing IR light). In the depicted embodiment, V-LEDs 151, IR-LEDs 153, and photodiodes 155 are substantially collocated with one another. Moreover, there are 16 sets of each of V-LEDs 151, IR-LEDs 153, and photodiodes 155 evenly (or in other embodiments unevenly) spaced around ring 160 (e.g., including the PCB discussed above) of dynamic illuminator 105. One of ordinary skill in the art will appreciate that dynamic illuminator 105 may take a number of shapes (other than a ring) and may include any number of V-LEDs 151, IR-LEDs 153, and photodiodes 155.

In one embodiment, the controller (e.g., controller 105) may fire all the IR-LEDs 153 in a clockwise pattern (e.g., 1-16) around dynamic illuminator 105, and then the controller may fire only some of the V-LEDs but similarly in a clockwise pattern (e.g., 1, 3, 5, 6, 8, 9, 11 etc.). Alternatively, the order of firing both IR-LEDs 153 and V-LEDs 151 may be random. While in some embodiments, the camera may be used to determine which IR-LEDs 153 produce reflection; as will be explained blow, in other embodiments, photodiodes 155 (and also the camera) may be used to determine the amount of reflection with less processing power.

Plurality of photodiodes 155 (e.g., GaAs based, Si based, or the like) may also be coupled to the controller (e.g., controller 155), and the controller causes dynamic illuminator 105 to perform operations including measuring, with the plurality of photodiodes, the amount of reflection of the infrared light from the eye. The controller may analyze the amount of reflection measured by the plurality of photodiodes to determine the amount of reflection of the infrared light from the eye for each of the IR-LEDs. In some embodiments, this may simply be a threshold level of reflectance, where if one of photodiodes 155 receives greater than a threshold level of IR light reflected from the eye, the controller will not turn on the corresponding V-LED during visible image capture. In some embodiments, photodiodes 155 may have color filters (e.g., polymer color filters, metal mesh, or the like) disposed over photodiodes 155 to allow IR and/or red light to pass to the photodiodes while blocking other wavelengths of light. Thus, other wavelengths of light that may cause errors in measurement of photodiodes 155 are removed.

Similarly, the controller may determine when the interior of the eye is in focus based on the amount of reflection of the infrared light from the eye, as measured with the plurality of photodiodes 155. This may be achieved with contrast detection autofocus or other techniques. Using photodiodes 155 to determine if the camera is in focus, may cut down on processing power required to autofocus. However, in other or the same embodiments, the controller analyzes the amount of IR reflection as measured by the camera to determine the amount of reflection of the infrared light from the eye for each of the IR-LEDs.

It is appreciated that in some embodiments, collocation may include "average co-location" for the IR and white LED's. Rather than co-locating the both sources, IR-LEDs 153 are disposed adjacent to the V-LEDs 151 (e.g., around the optical diameter) which effectively acts as the same space (e.g., a shift in X, Y location may be somewhat compensated by putting the LED's on the same diameter since the optical system is symmetric). This is depicted in the "alternate diode configuration". One of ordinary skill in the art having the benefit of the present disclosure will appreciate that other diode configurations (not depicted) are contemplated.

One of ordinary skill in the art will appreciate that the diodes (V-LEDs and IR-LEDs) depicted in FIGS. 1A and 1B are just one embodiment of "light emitters" that may be used to illuminate the eye. Other light sources such as flash bulbs, lasers or the like may be used. Additionally, it is not necessary to use just visible and IR light. V-LEDs may be replaced with nonvisible light emitters (NV-LEs) or other light emitters (LEs) that may emit visible light. Also IR-LEDs may be replaced with other NV-LEs that produce other nonvisible wavelengths of light (e.g., low-energy ultraviolet, or the like).

Figure 1C:
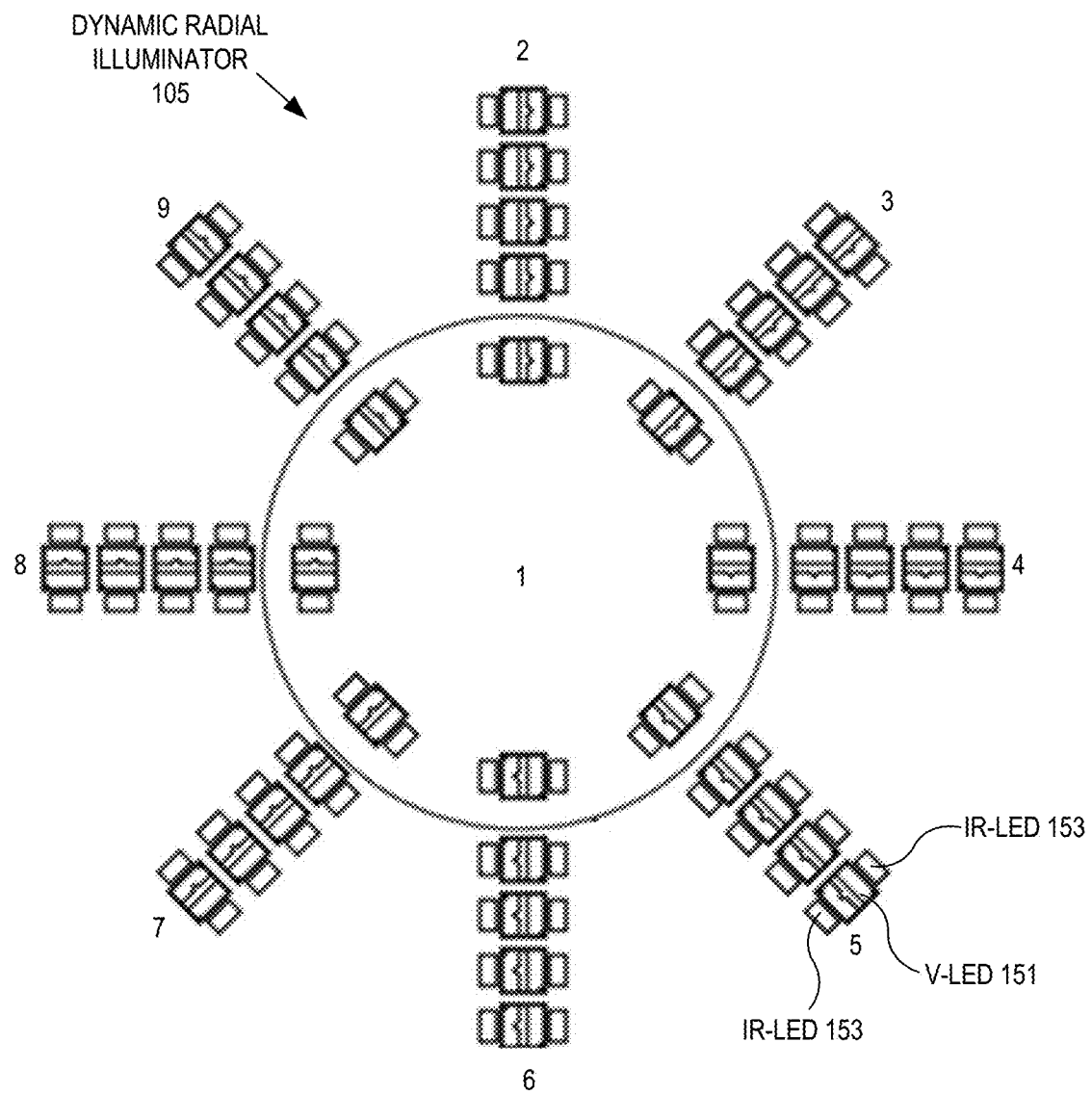
FIG. 1C illustrates a frontal view of a dynamic illuminator included in the apparatus of FIG. 1A, in accordance with an embodiment of the disclosure.

FIG. 1C illustrates a frontal view of a dynamic illuminator 105 included in the apparatus of FIG. 1A, in accordance with an embodiment of the disclosure. As shown, dynamic illuminator 105 in FIG. 1C has many of the same components as the dynamic illuminator depicted in FIG. 1B. However, in FIG. 1C, two IR-LEDs 153 are disposed on either side of each V-LED 151. Additionally, here, IR-LEDs 153 and V-LEDs 151 disposed in the inner circle may fire first (either all at once or individually), followed by sequential firing of the lines of LEDs disposed outside the inner circle (e.g., line 2, line 3, line 4, etc.). One of ordinary skill in the art will appreciate that the LEDs in the lines depicted may fire in any order (e.g., sequentially, randomly, or the like), and that the order of LED firing described here is merely to illustrate several examples. Additionally, it is appreciated that not all of the light emitters may be disposed on the same Z plane (in and out of the page), for example visible light emitters may be disposed closer to the eye than the non-visible light emitters, or vice versa.

In the depicted example, a pupil camera (which may be included in the same camera as camera 110 in FIG. 1A, or a separate discrete camera), may determine the position of the pupil prior to illuminating the eye with either IR-LEDs 153 or V-LEDs 151. The pupil camera may provide information about the location of the pupil to the system/controller, and the system selects the LEDs that are likely to obtain the best illumination conditions based, at least in part, on the pupil location. Subsequently, the system can illuminate the eye with fewer light emitters when capturing the images of the interior of the eye.

In some embodiments, while IR-LEDs 153 and V-LEDs 151 are collocated, non-visible light emitters (e.g., IR-LEDs 153) may be mapped to light emitters (e.g., V-LEDs 151) that are not collocated. For example, reflectance generated by an IR-LED 153 in row 3 may be a better indication of visible reflectance generated by a V-LED in row 4 (due to the different focal lengths of the light emitted from the IR-LEDs 153 and V-LEDs 151). Accordingly, a lookup table or the like may be used to determine which non-visible light emitter(s) should be used to illuminate the eye in order to obtain an accurate prediction of visible reflection from visible light emitters. As stated, in this embodiment, the non-visible light emitters used to illuminate the eye need not be collocated with the visible light emitters.

Figure 2:
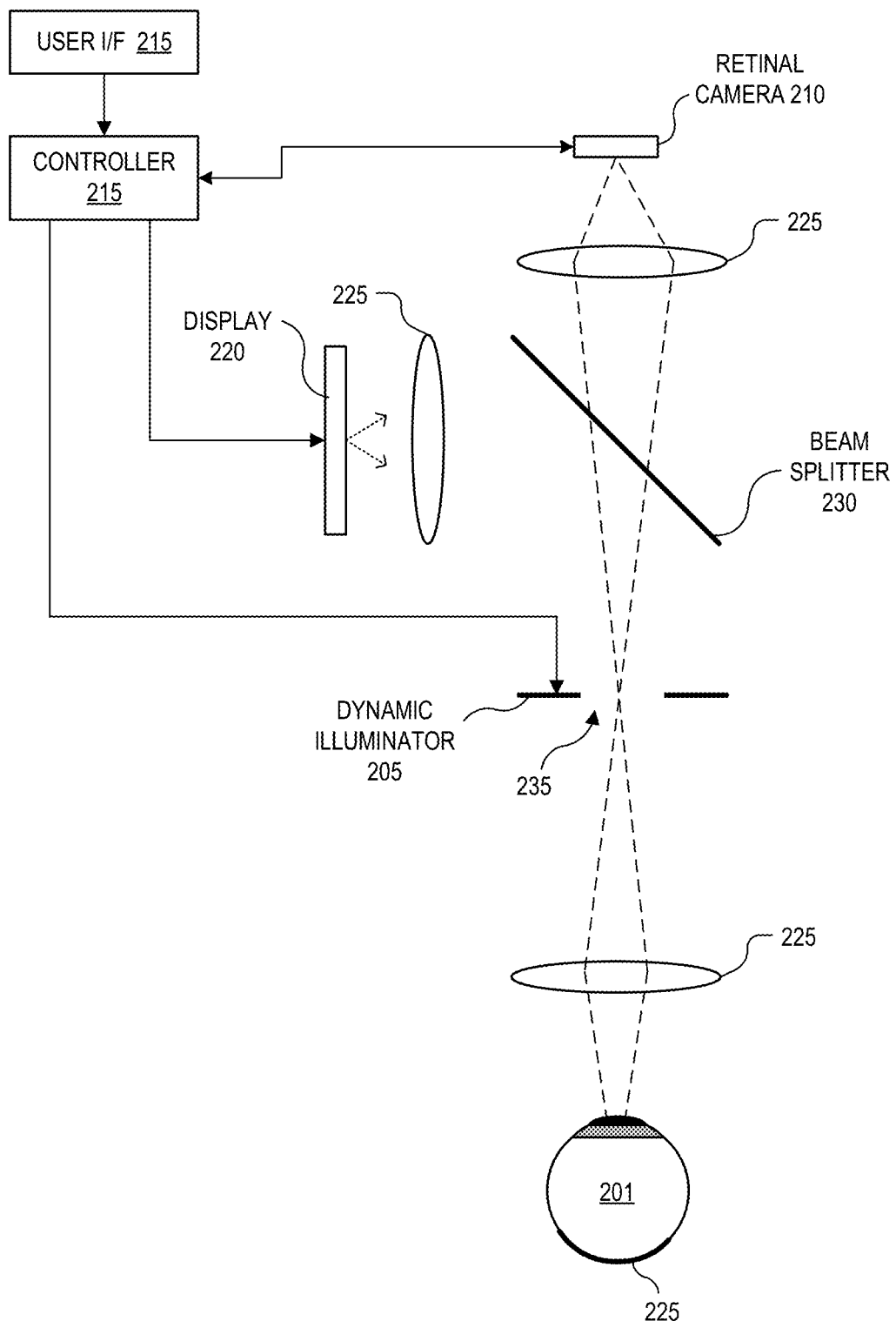
FIG. 2 is a diagram illustrating a demonstrative retinal imaging system using a dynamic illuminator, in accordance with an embodiment of the disclosure.

FIG. 2 is a diagram illustrating a demonstrative retinal imaging system 200 using a dynamic illuminator 205, in accordance with an embodiment of the disclosure. Retinal imaging system 200 is one possible (more complex) implementation of system 100. The illustrated embodiment of retinal imaging system 200 includes a dynamic radial illuminator 205, retinal camera 210, controller 215, user interface 215, display 220, and an optical relay system that includes lenses 225 and a beam splitter 230. System 200 operates in the same manner as described in connection with system 100.

A central section 235 of dynamic illuminator 205 is physically positioned in the optical path about the field of view (FOV) of retinal 225. In some embodiments, the annular region of dynamic illuminator 205 operates as a stop to block many off-axis deleterious reflections before reaching retinal camera 210. The retinal images are passed through central section 235 to retinal camera 210. In addition to reducing image artifacts due to deleterious reflections from the cornea, the use of multiple illumination locations about the annular region of dynamic illuminator 205 also serves to increase the eyebox of system 200. The eyebox is the region in space where eye 201 can be located and imaged. In some embodiments, all or some of discrete light sources of dynamic illuminator 205 are disposed outside (e.g., peripheral to) a perimeter of the imaging path extending from retina 225 to retinal camera 210. In other embodiments, one or more of the discrete light sources of dynamic illuminator 205 are disposed inside the perimeter of the imaging path to retinal camera 210.

Beam splitter 230 (or polarizing beam splitter) is positioned to pass a portion of the light of retinal images to retinal camera 210 while reflecting display light output from display 220 to eye 201. The display light may include a fixation target or other visual stimuli to aid retinal alignment during imaging. In some embodiments, beam splitter 230 is more transmissive than reflective. In one embodiment, beam splitter 230 is approximately 90% transmissive and 10% reflective. Other reflectance/transmittance ratios may be implemented. Lenses 225 are provided throughout system 200 to provide image and light focusing in the optical paths. User interface 215 provides a mechanism to commence burst image capture. In one embodiment, user interface 215 is a button, touch screen, mouse or the like.

Figure 3:
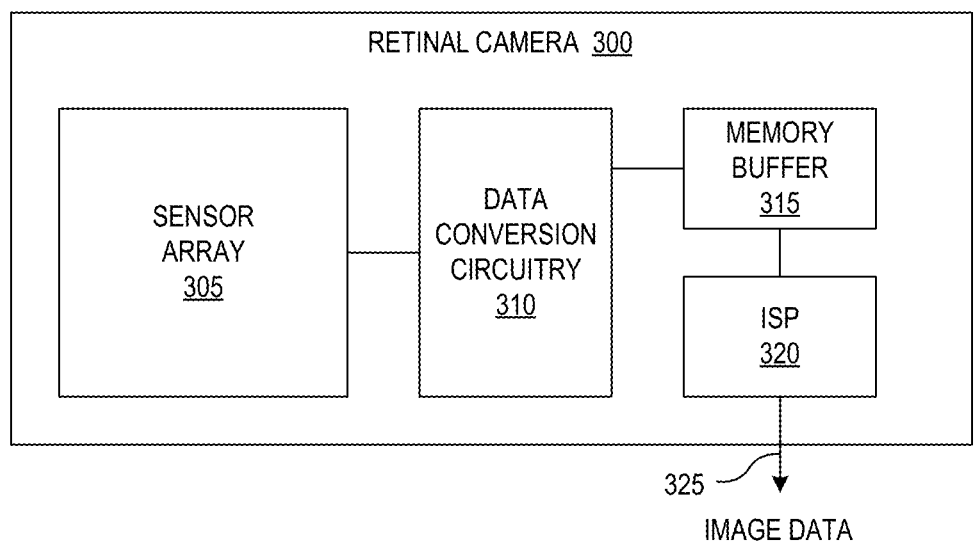
FIG. 3 is a functional block diagram of a retinal camera including an integrated image signal processor, in accordance with an embodiment of the disclosure.

FIG. 3 is a functional block diagram of a retinal camera 300 including an integrated image signal processor, in accordance with an embodiment of the disclosure. Retinal camera 300 is one possible implementation of retinal camera 110 (or 210). The illustrated embodiment of retinal camera 300 includes a two-dimensional sensor array 305, data conversion circuitry 310, a memory buffer 315, an integrated image signal processor (ISP) 320, and an output port 325.

During operation, two-dimensional image data (e.g., retinal images) is acquired by sensor array 305 and converted from the analog domain to the digital domain by data conversion circuitry 310. The image data may be acquired at a high frame rate (e.g., 24, 48, 60, 240, 1000 frames per second) and stored into memory buffer 315. ISP 320 operates on the buffered retinal image frames to identify useable or defect regions, annotate the regions of interest in the image frames, and/or combine the useable regions into high quality, composite retinal images. Accordingly, in one embodiment, some of the image processing tasks described above may be off-boarded to ISP 320 from controller 315. ISP 320 may be considered a logical subcomponent of controller 315.

Figure 4:
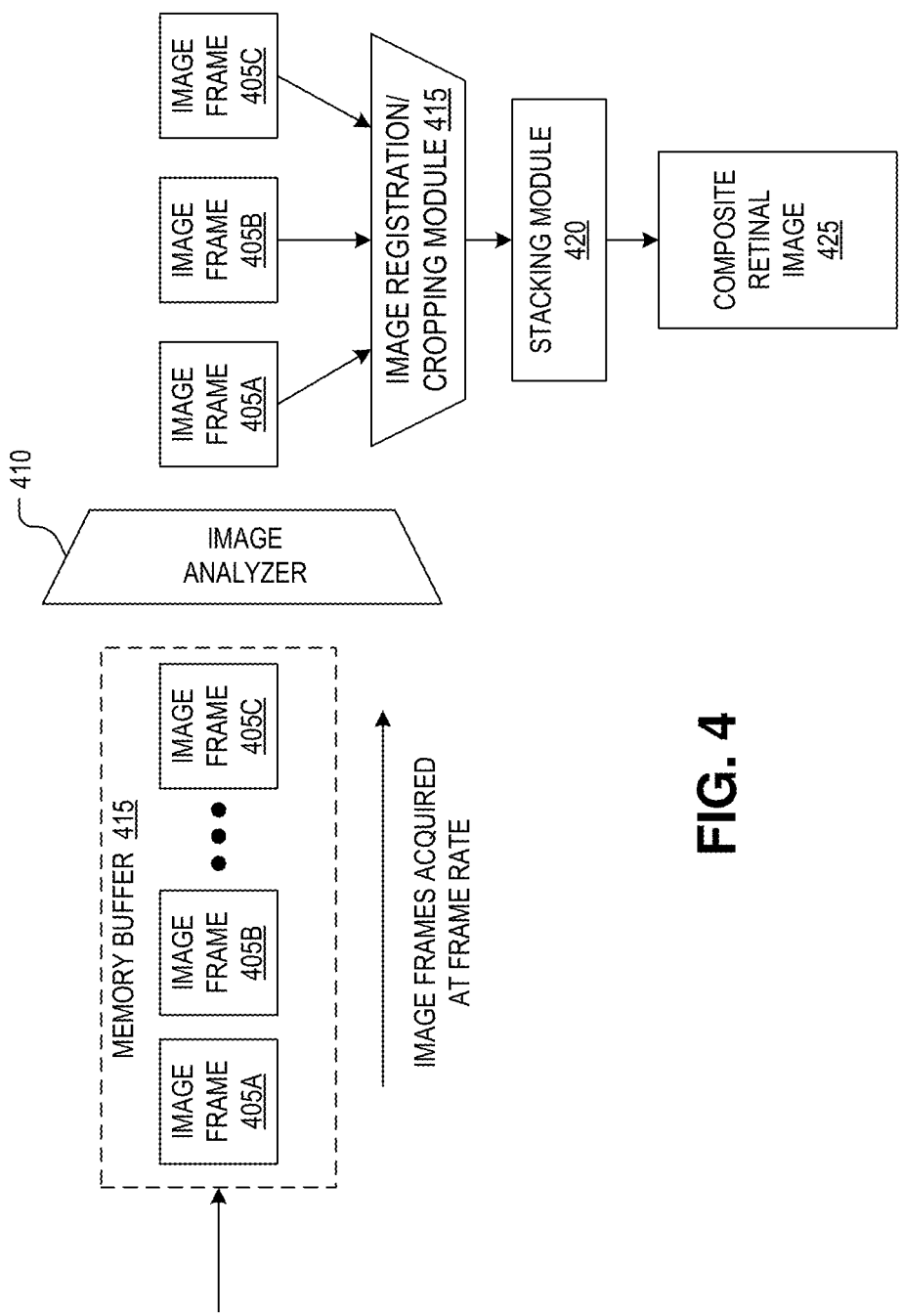
FIG. 4 is a block flow diagram illustrating image processing by a retinal camera including an integrated image signal processor, in accordance with an embodiment of the disclosure.

FIG. 4 is a block flow diagram illustrating image processing by a retinal camera (e.g., retinal camera 300 of FIG. 3) including an integrated image signal processor (e.g., ISP 320 of FIG. 3), in accordance with an embodiment of the disclosure. As illustrated, image frames 405A-C of a retina are acquired by a sensor array (e.g., sensor array 305 of FIG. 3) at a high frame rate, converted into the digital domain by data conversion circuitry (e.g., data conversion circuitry 310 of FIG. 3), and buffered into a memory buffer (e.g., into memory buffer 315 of FIG. 3). An image analyzer 410 is executed by the ISP to analyze the buffered retinal images 405 (a sort of preprocessing) to determine which portions of images frames are of sufficient quality and which are of insufficient quality due to unacceptable image artifacts. For example, image analyzer 410 may analyze image frames 405 for blurred portions, portions that do not have sufficient contrast to be useful, are washed out, and/or include unacceptable corneal or iris reflections, or lens flare. Image portions that are deemed unacceptable are flagged unacceptable (e.g., marked or annotated) while image portions that are deemed acceptable are flagged as such. The image frames are then registered to each other (e.g., pixel-to-pixel alignment), cropped to a common FOV by image registration/cropping module 415, and then combined by stacking module 420 into a single composite retinal image 425. Stacking module 420 may combine images to generate high dynamic range images. In other embodiments, image frames 405 are simply combined without analysis and/or annotation of the individual image frames. All image processing steps and hardware discussed in connection with FIGS. 3 and 4 can be considered part of a "controller" in accordance with the teachings of the present disclosure.

Figure 5A:
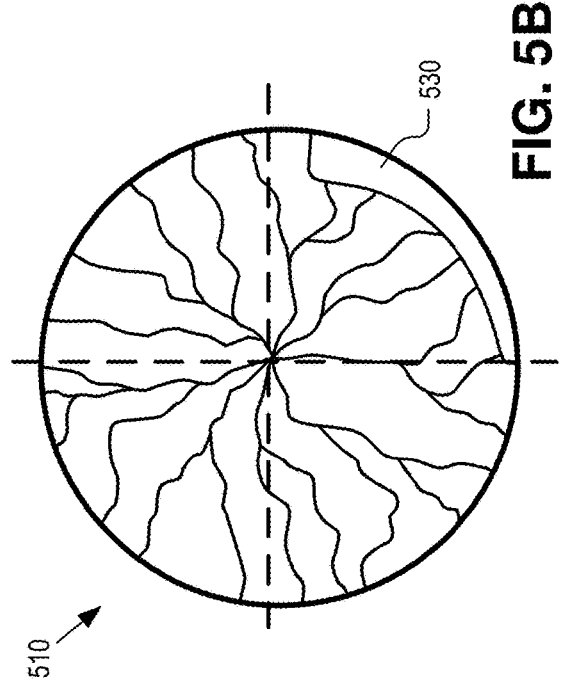
FIGS. 5A-5C illustrate image frames of a retina captured with different illumination patterns, in accordance with an embodiment of the disclosure.
Figure 5B:
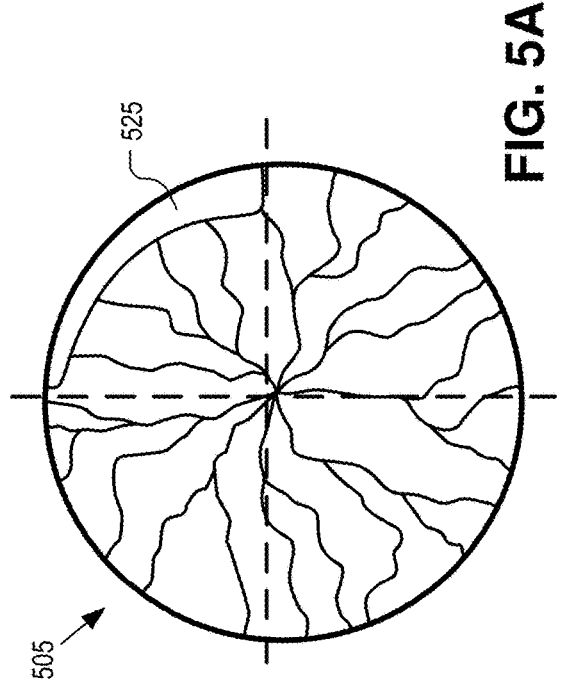
Figure 5C:
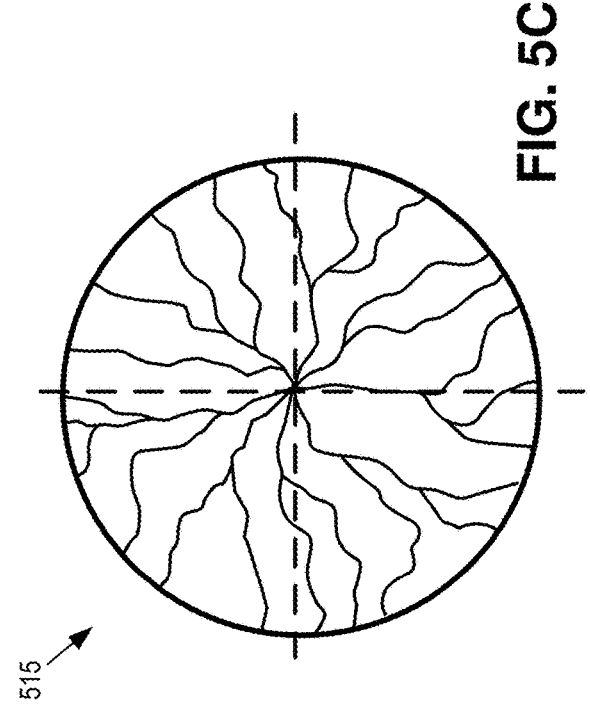

FIGS. 5A-5C illustrate image frames of a retina captured with different illumination patterns, in accordance with an embodiment of the disclosure. For example, FIG. 5A illustrates an example image frame 505 of retina 525 having an image artifact 525 in the upper right quadrant of the image. This may be an image captured by the camera after IR illumination with an IR-LED located proximate to the upper right hand corner of the eye. Image artifact 525 may be a corneal reflection, a reflection or obstruction due to iris, lens flare, or otherwise. Accordingly, the upper right quadrant of image frame 505 may be deemed an unacceptable defect region. Thus, the eye may be illuminated by a V-LED that is not located proximate to the upper right hand corner. Correspondingly, the lower right quadrant of image frame 510, which includes image artifact 530, may be deemed to be a defect region. Image frame 510 may have been illuminated with an IR-LED located proximate to the bottom right-hand corner. Accordingly, the eye will not be illuminated with the corresponding V-LED. Image frame 515 appears to have no defects. Image frame 515 may have been illuminated by an IR-LED disposed proximate to the lower left-hand corner of the eye. Accordingly, the controller may instruct the V-LEDs in the lower right hand corner of the eye to flash while capturing the visible images of the eye.

FIG. 6 illustrates focus stacking images of an iris, in accordance with an embodiment of the disclosure. As shown, four image frames (605A-605D) of a retina are captured with an image sensor. Long lines represent fully resolved veins and other anatomical structures in/on the retina; short dashed lines represent out-of-focus or washed out portions of the image. As shown, the lower left hand corner of image frame 605A is fully resolved, but the rest of the image is not. Similarly, the middle portion (extending from the upper left-hand corner of the frame to the bottom right-hand corner) of image frame 605B is in focus and fully resolved, but the rest of image frame 605B is not. The upper right-hand corner of image frame 605C is in focus, but the rest of the image is not. Lastly, image frame 605D is out of focus and contains no useful information. Accordingly, image frame 605D is removed, and not sent to stacking module 620 for use in composite image 625. The rest of image frames 605A-605C are sent to stacking module 620 to be combined into a single high-resolution composite image 625 with a large depth of field. In one embodiment, images may be combined using edge detection, feature detection, or Fourier analysis.

Figure 7:
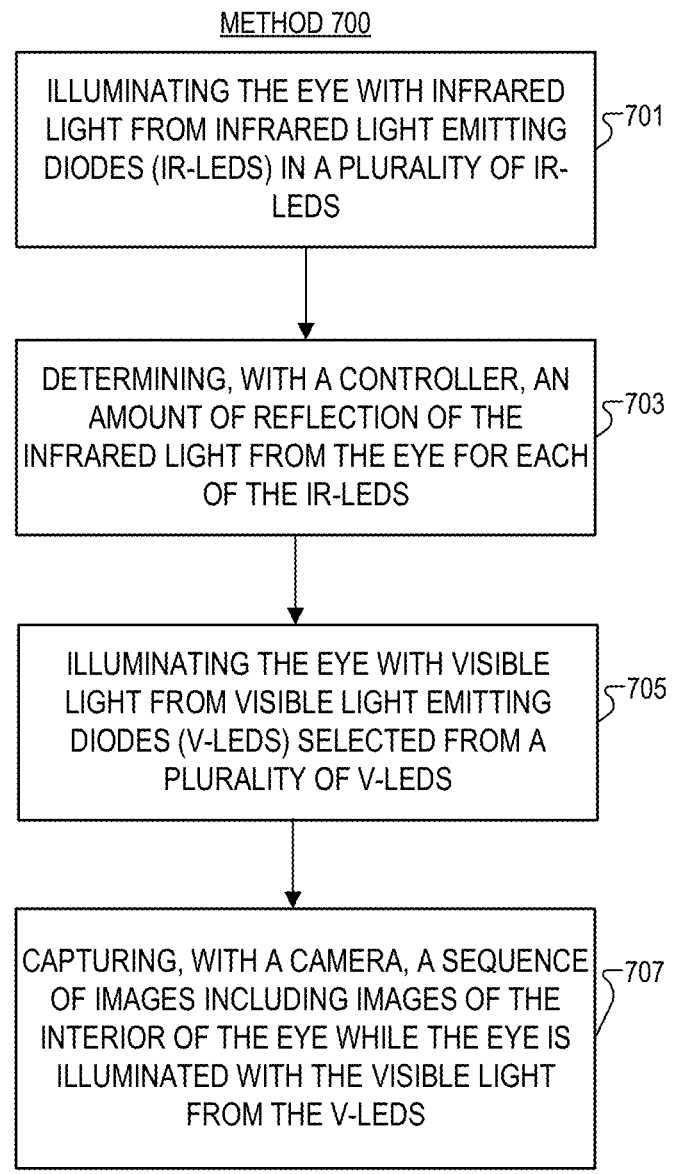
FIG. 7 illustrates a flow chart for a method of imaging an interior of an eye, in accordance with an embodiment of the disclosure.

FIG. 7 illustrates a flow chart for a method 700 of imaging an interior of an eye, in accordance with an embodiment of the disclosure. It is appreciated that blocks (e.g., blocks 701-707) in method 700 may occur in any order and even in parallel. Moreover, blocks maybe added to, or removed, from method 700 in accordance with the teachings of the present disclosure.

Block 701 shows illuminating the eye with infrared light from infrared light emitting diodes (IR-LEDs) in a plurality of IR-LEDs. This may occur by sequentially turning on and off IR-LEDs. Alternatively, groups of IR-LEDs may be turned on and off simultaneously. One of ordinary skill in the art will appreciate that IR-LEDs may be turned on and off in any order and even in parallel. Moreover, the eye may be illuminated by both IR-LEDs and V-LEDs at the same time.

Block 703 illustrates determining, with a controller, an amount of reflection of the infrared light from the eye for each of the IR-LEDs. In one embodiment determining may include measuring the light reflected back (e.g., how much IR light is reflected back to the image sensor, relative to the other IR-LEDS, using saturation level of camera or photodiodes). The controller may correlate the amount of reflection of the infrared light from the eye for each of the IR-LEDs with a second amount of reflection of the visible light from the eye for each of the V-LEDs. In other words, the controller may know what quantity of IR reflection corresponds to a specific level of visible reflection (e.g., via a look-up table or the like). In some embodiments, the eye may be illuminated with the infrared light before illuminating the eye with the visible light; however, in other embodiments the opposite may be true.

In some embodiments, the system may include a plurality of photodiodes and the plurality of photodiodes measure the amount of reflection of the infrared light from the eye for each of the IR-LEDs. Each of the photodiodes in the plurality of photodiodes may be collocated with each of the IR-LEDs and each of the V-LEDs.

Block 705 discloses illuminating the eye with visible (e.g., white light, blue light, green light, red light, or any combination thereof) light from visible light emitting diodes (V-LEDs) selected from a plurality of V-LEDs based on the amount of reflection of the infrared light for each of the IR-LEDs. In some embodiments, illuminating the eye with visible light from the visible light emitting diodes (V-LEDs) includes disabling some of the V-LEDs when the amount of reflection of the infrared light from a corresponding IR-LED is greater than a threshold reflectance value Moreover the controller may determine an order of the V-LEDs to illuminate the eye with, based on the amount of reflection of the infrared light. The order and timing of when V-LEDs are activated may be used to further mitigate reflections in the images.

Block 707 shows capturing, with a camera, a sequence of images including images of the interior of the eye while the eye is illuminated with the visible light from the V-LEDs. In some embodiments the system may continue flash optimization after the V-LEDs start firing. In some embodiments, either the photodiodes or camera may be used to capture reflected IR light and determine that the camera is in focus to capture the sequence of images using contrast detection autofocus. In some embodiments this may include measuring, with the controller, an intensity difference of the infrared light between the photodiodes, or an intensity difference of the infrared light between adjacent pixels in the camera, depending on if the camera or the photodiodes are used to autofocus the camera.

After capturing the series of images, at least some of the images in the sequence of images may be combined using the controller to form a composite image of the interior of the eye, and combining includes at least one of focus stacking, image stitching, image blending, or any combination thereof.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for imaging an interior of an eye, comprising:
    a light sensitive sensor;
    a plurality of light emitters (LEs) capable of outputting visible light;
    a plurality of nonvisible light emitters (NV-LEs) capable of outputting nonvisible light; and
    a controller coupled to the plurality of LEs, the plurality of NV-LEs, and the light sensitive sensor, wherein the controller implements logic that when executed by the controller causes the apparatus to perform operations including:
        illuminating the eye with the nonvisible light from the plurality of NV-LEs;
        determining an amount of reflection of the nonvisible light from the eye for each of the NV-LEs in the plurality of NV-LEs;
        selecting one or more of the LEs in the plurality of LEs based at least in part on the amount of reflection of the nonvisible light for each of the NV-LEs;
        illuminating the eye with the visible light from the selected one or more of the LEs in the plurality of LEs; and
        capturing, with the light sensitive sensor, a sequence of images of the interior of the eye while the eye is illuminated with the visible light from the selected one or more of the LEs.

2. The apparatus of claim 1, wherein each of the LEs is collocated with each of the NV-LEs, and wherein the controller further implements logic that when executed by the controller causes the apparatus to perform operations including:
    correlating the amount of reflection of the nonvisible light from the eye for each of the NV-LEs with a second amount of reflection of the visible light from the eye for each of the LEs.

3. The apparatus of claim 2, wherein illuminating the eye with a selected one or more of the LEs includes disabling some of the LEs when the amount of reflection of the nonvisible light from a corresponding NV-LE is greater than a threshold reflectance value.

4. The apparatus of claim 1, further comprising a plurality of photodiodes coupled to the controller, wherein the controller further implements logic that when executed by the controller causes the apparatus to perform operations including:
    measuring, with the plurality of photodiodes, the amount of reflection of the nonvisible light from the eye, wherein the controller analyzes the amount of reflection measured by the plurality of photodiodes to determine the amount of reflection of the nonvisible light from the eye for each of the NV-LEs.

5. The apparatus of claim 4, wherein the controller further implements logic that when executed by the controller causes the apparatus to perform operations including:
    determining when the interior of the eye is in focus based on the amount of reflection of the nonvisible light from the eye, as measured with the plurality of photodiodes.

6. The apparatus of claim 1, wherein the controller further implements logic that when executed by the controller causes the apparatus to perform operations including:
    measuring, using the light sensitive sensor, the amount of reflection of the nonvisible light from the eye, wherein the controller analyzes the amount of reflection measured by the light sensitive sensor to determine the amount of reflection of the nonvisible light from the eye for each of the NV-LEs.

7. The apparatus of claim 6, wherein the controller further implements logic that when executed by the controller causes the apparatus to perform operations including:
    determining when the interior of the eye is in focus based on the amount of reflection of the nonvisible light from the eye, as measured by the light sensitive sensor.

8. The apparatus of claim 1, wherein the controller further implements logic that when executed by the controller causes the apparatus to perform operations including:
    combining at least some of the images in the sequence of images to form a composite image of the interior of the eye, wherein combining includes at least one of focus stacking, image stitching, image blending, or any combination thereof.

9. The apparatus of claim 1, wherein illuminating the eye with the nonvisible light from the NV-LEs includes sequentially illuminating the eye with each of the NV-LEs in the plurality of NV-LEs, and wherein illuminating the eye with the visible light from LEs includes sequentially illuminating the eye with some of the LEs in the plurality of LEs.

10. The apparatus of claim 9, wherein the controller further implements logic that when executed by the controller causes the apparatus to perform operations including:
    determining an order of the LEs to illuminate the eye with, in response to the amount of reflection of the nonvisible light from the eye for each of the NV-LEs.

11. The apparatus of claim 1, wherein the plurality of LEs and the plurality of NV-LEs are disposed on a ring, and wherein each of the LEs and each of the NV-LEs are disposed adjacent to each other and evenly spaced around the ring.

12. A method of imaging an interior of an eye, comprising:
    illuminating the eye with nonvisible light from nonvisible light emitters (NV-LEs) in a plurality of NV-LEs;
    determining, with a controller, an amount of reflection of the nonvisible light from the eye for each of the NV-LEs;
    selecting light emitters (LEs) from a plurality of LEs based on the amount of reflection of the nonvisible light for each of the NV-LEs;
    illuminating the eye with visible light from selected ones of the LEs; and capturing, with a light sensitive sensor, a sequence of images including images of the interior of the eye while the eye is illuminated with the visible light from the selected ones of the LEs.

13. The method of claim 12, further comprising correlating, with the controller, the amount of reflection of the nonvisible light from the eye for each of the NV-LEs with a second amount of reflection of the visible light from the eye for each of the LEs.

14. The method of claim 13, wherein illuminating the eye with light from the LEs includes disabling some of the LEs when the amount of reflection of the nonvisible light from a corresponding NV-LE is greater than a threshold reflectance value.

15. The method of claim 12, further comprising determining an order of the LEs to illuminate the eye with, based on the amount of reflection of the nonvisible light.

16. The method of claim 12, further comprising combining, with the controller, at least some of the images in the sequence of images to form a composite image of the interior of the eye, wherein combining includes at least one of focus stacking, image stitching, image blending, or any combination thereof.

17. The method of claim 16, wherein the composite image includes an image of the eye's retina.

18. The method of claim 12, wherein illuminating the eye with the nonvisible light occurs before illuminating the eye with the visible light, and wherein each of the NV-LEs is collocated with each of the LEs.

19. The method of claim 12, further comprising measuring, with a plurality of photodiodes, the amount of reflection of the nonvisible light from the eye for each of the NV-LEs.

20. The method of claim 19, further comprising determining that the light sensitive sensor is in focus to capture the sequence of images using contrast detection autofocus.

21. The method of claim 19, wherein measuring the amount of reflection of the nonvisible light includes filtering wavelengths of light other than the nonvisible light with color filters disposed over the plurality of photodiodes.

22. The method of claim 20, wherein using contrast detection autofocus includes measuring, with the controller, an intensity difference of the nonvisible light between photodiodes.

23. The method of claim 20, wherein using contrast detection autofocus includes using the controller to determine an intensity difference of the nonvisible light between adjacent pixels in the light sensitive sensor.

24. The method of claim 12, further comprising:
capturing an image of a pupil of the eye prior to selecting the LEs from the plurality of LEs; and
determining with the controller a location of the pupil using the image or the pupil, and wherein selecting the LEs includes using, at least in part, the location of the pupil to select the LEs.

25. The method of claim 12, wherein at least some of the selected LEs are not collocated with each of the NV-LEs used to illuminating the eye.

* * * * *